United States Patent [19]
Northam et al.

[11] Patent Number: 5,593,880
[45] Date of Patent: Jan. 14, 1997

[54] DUAL-STATE NUTRITIONAL MEDIUM FOR THE TRANSPORT AND MAINTENANCE OF CELLS

[75] Inventors: William J. Northam, San Antonio; John D. Barry, Boerne; Richard L. Heberling, San Antonio, all of Tex.

[73] Assignee: Viratest International, Inc., San Antonio, Tex.

[21] Appl. No.: 194,575

[22] Filed: Feb. 10, 1994

[51] Int. Cl.⁶ .............................. C12N 5/02; C12M 1/18; C12M 1/16; A01N 1/02
[52] U.S. Cl. .................. 435/240.1; 435/1.1; 435/240.2; 435/240.4; 435/240.3; 435/240.54; 435/260; 435/305.2; 435/305.3; 435/305.4; 435/307.1
[58] Field of Search ...................... 435/240.2, 240.3, 435/240.31, 240.4, 240.45, 240.54, 240.1, 1, 299, 300, 301, 260, 177

[56] References Cited

U.S. PATENT DOCUMENTS

| | | | |
|---|---|---|---|
| 4,148,689 | 4/1979 | Hino et al. | 435/173 |
| 5,004,805 | 4/1991 | Gohda et al. | 530/399 |
| 5,045,454 | 9/1991 | Bertheussen | 435/240.31 |
| 5,157,110 | 10/1992 | Kotwal et al. | 530/350 |
| 5,314,814 | 5/1994 | Harder et al. | 435/177 |

OTHER PUBLICATIONS

*ATCC Catalogue of Cell Lines & Hybridomas.* 6th Edition. 1988 pp. i–xii.

Primary Examiner—Irene Marx
Assistant Examiner—L. Blaine Lankford
Attorney, Agent, or Firm—Loeb & Loeb LLP

[57] ABSTRACT

A nutritional medium for enabling the growth, maintenance and transport of cells in a container of virtually any size or shape, including a substantially flat, multi-well plastic plate. The nutritional medium is capable of assuming a substantially liquid state above a first temperature and a substantially solid state below a second temperature. Both the first and second temperatures are generally compatible with the survival of the cells in the container. The cells are covered with the medium while the medium is in a substantially liquid state, and the temperature of the medium is then reduced to a temperature at which the medium assumes a substantially solid state. The medium is maintained in a substantially solid state while the cells are transported. Upon arrival at the end user, the temperature of the medium is increased to a temperature at which the medium assumes a substantially liquid state. Following a change to fresh maintenance medium, the cells in the container are ready for immediate use.

14 Claims, 1 Drawing Sheet

SPECIMEN NUMBER: 1 2 3 4 5 6

CELL TYPE:
- MRC-5
- HF
- A549
- VERO

Cell monolayer
CELLo-GEL (volume depending upon well size)

DUAL-STATE NUTRITIONAL MEDIUM FOR THE TRANSPORT AND MAINTENANCE OF CELLS

BACKGROUND OF THE INVENTION

1. Field of the Invention

The present invention relates to a dual-state nutritional medium for the transport and maintenance of cells, and a method of using the same.

2. Description of Related Art

Growing and maintaining living cells outside the original host source is achieved by cell (or tissue) culture. Living cells outside the original host source may be maintained in vitro through numerous passages if prepared and provided with the appropriate nutrients. The nutrients required for the successful culture of cell lines have been established by many laboratories over at least the past fifty years. As a result, literally thousands of different cell lines have been initiated from the tissues of different species of animals, birds, insects, and plants, and are now in use in laboratories throughout the world.

Regardless of the cell system involved, the growth pattern of virtually all cells in culture is basically the same. Cell growth is dependent upon an appropriate nutrition and support system. Although cells may be grown successfully as a suspension, most cell cultures are preferentially grown as monolayers attached to a solid surface. This type of culture is particularly useful in the virus laboratory, but is also used in other disciplines. Cell cultures may be grown in either test tubes, flasks, or in wells of multi-well plastic plates. The most commonly used material for these containers is polystyrene. When appropriately treated, polystyrene supports the growth of cells in culture as monolayers on its surface.

Laboratories must utilize numerous cell lines from various origins for testing, since no single cell type is sensitive to all viruses. Many of the animal and plant cell cultures currently being used in laboratories are prepared in and obtained from other laboratories or commercial sources. The continued availability of cells to those laboratories without the capability of satisfying their cell culture needs is therefore very important. Such laboratories require cells from outside sources. These cells may be primary (first passage from the host) or serial (two or more passages from the original host). Regardless of passage number, to be useful, cell monolayers must be viable, albeit physiological changes from their in vivo state may occur.

At present, there are essentially two methods for obtaining monolayer cultures in multi-well plates for use in the laboratory. In the first method, cell cultures are transported as monolayers with a liquid medium filling the shipping container. In the second method, cell cultures are transported as cell suspensions. Both methods require that the shipping container be sealed to prevent loss of fluid. Neither method permits shipping of cells in open, multi-well plates or other unsealed containers, such as petri dishes.

Upon receipt of the cells by the end user, the cells must be seeded into appropriate culture plates and allowed to grow to the desired density before the cells can be used. This seeding and growth process requires an additional three to five days, requires additional effort on the part of the end user, and increases the possibility of cell contamination with extraneous microorganisms. The predominant use of cells is in the form of cultivated cell monolayers grown on the bottom of wells in polystyrene plates of various sizes (6, 12, 24, 48, or 96 wells per plate) previously seeded with cells in suspension. These plates come with a loosely fitting lid which allows gaseous exchange with the surrounding environment but which does not seal the plate. Once formed from the seeded cells, the cell monolayers must be covered with a liquid growth or maintenance medium. In this form, the monolayers in the wells are ready for use. Some cells may grow in forms other than monolayers, but if their growth is by adherence to the surface of the wells, the requirements for viable shipping needs are similar.

Currently, laboratories desiring such monolayers in multi-well plates must first obtain or produce cells in flasks or bottles. After disrupting the cell monolayer, the wells are seeded with cells and allowed to grow to a desired number (generally sufficient to cover the bottom of the well surface). Then, when ready (several days after seeding) the study material is inoculated. This procedure is both labor intensive and time consuming. If laboratories desiring such cell monolayers could obtain cell cultures in flat multi-well plates in a ready to use form, then much time and effort would be reduced. However, shipment of cell monolayers in wells using a liquid medium as a cover presents a problem, since shipment causes the liquid medium to spill and causes cellular disruption.

Attempts have been made to ship cell cultures in multi-well plates by sealing the wells with an adhesive or plastic sheet or plugging the wells with a stopper. These techniques have several drawbacks. A strip "sealing" cap is only practical for use in plates containing relatively small wells (e.g. those with 96 wells). Such a strip sealing cap is generally ineffective to prevent bubbles and other damage to cells caused by continuous fluid motion. The use of small plastic plugs as stoppers to stop the wells does not protect cells from damage due to bubbles and movement of the medium during transit. Plastic adhesive sheets are available for sealing the wells in a multi-well plate, but toxicity of the adhesive prevents their general use. These sheets also do not prevent bubble formation nor liquid movement during transport.

It is an object of the present invention to overcome the above-described difficulties and to provide a system and process by which cells may be transported and be ready for use by the end user virtually immediately upon receipt.

SUMMARY OF THE INVENTION

In accordance with the present invention, these and other objectives are achieved by providing a nutritional medium for enabling the growth, maintenance and transport of cells in a container. The type of container used with the present invention may be of virtually any size or shape, and in particular may include a substantially flat, multi-well plastic plate. The nutritional medium provided herein is capable of assuming a substantially liquid state above a first temperature and a substantially solid state below a second temperature. Both the first and second temperatures are generally compatible with the survival of the cells in the container. The cells are covered with the medium while the medium is in a substantially liquid state, and the temperature of the medium is then reduced to a temperature at which the medium assumes a substantially solid state. The medium is maintained in a substantially solid state while the cells are transported. Upon arrival at the end user, the temperature of the medium is increased to a temperature at which the medium assumes a substantially liquid state. Following a change to fresh maintenance medium, the cells in the container are thereby ready for virtually immediate use.

A dual-state transport medium in accordance with the present invention presents a number of advantages. For example, cells shipped in accordance with the present invention may be transported over long distances with virtually no adverse effects or medium spillage. Cells shipped in accordance with the present invention are ready for virtually immediate use upon arrival at their destination, without loss of viability and without requiring additional cell culture propagation prior to use. Alternatively, cells shipped in accordance with the present invention may be stored for up to at least seven days at 4°–8° C. in an ambient air atmosphere.

The present invention makes it possible to utilize cell containing vessels in multiple configurations. The present invention allows the shipment of cell cultures in multi-well plates, thereby eliminating the need for handling multiple single, screw capped tubes. The present invention has the ability to maintain and transport an unlimited number of different cell types as well as transport different cell lines in the same carrier plate. When using cell cultures in tubes, a dual-state medium in accordance with the present invention may be added to the upper limit of cell growth in the tube. This enables transport in test tube cultures without cellular disruption due to medium agitation and bubble formation.

The present invention may be used to transport cell cultures in a variety of carriers in addition to multi-well polystyrene plates. For example, cell cultures may be transported in previously seeded tubes, flasks or bottles, vials or petri dishes. The present invention is useful in protecting cells from damage due to bubbles and movement of the medium during transit, even in carriers (such as sealed flasks) in which spillage is not a problem.

A transport medium in accordance with the present invention presents many advantages over the plastic strip caps and adhesive covers known in the prior art. A transport medium in accordance with the present invention is a nontoxic cell supporting medium, holding the cells and fluid medium in place because of the gelatin content, but it also eliminates fluid motion during transport, subsequent bubble formation and possible toxicity. In as much as a dual-state transport medium in accordance with the present invention contains a suitable growth and maintenance medium as its base, the cells are maintained in good physiological condition and are ready for use upon receipt.

BRIEF DESCRIPTION OF THE DRAWINGS

A detailed description of a preferred embodiment of the invention will be made with reference to the accompanying drawings.

DETAILED DESCRIPTION OF A PREFERRED EMBODIMENT

Figures 1, 2:
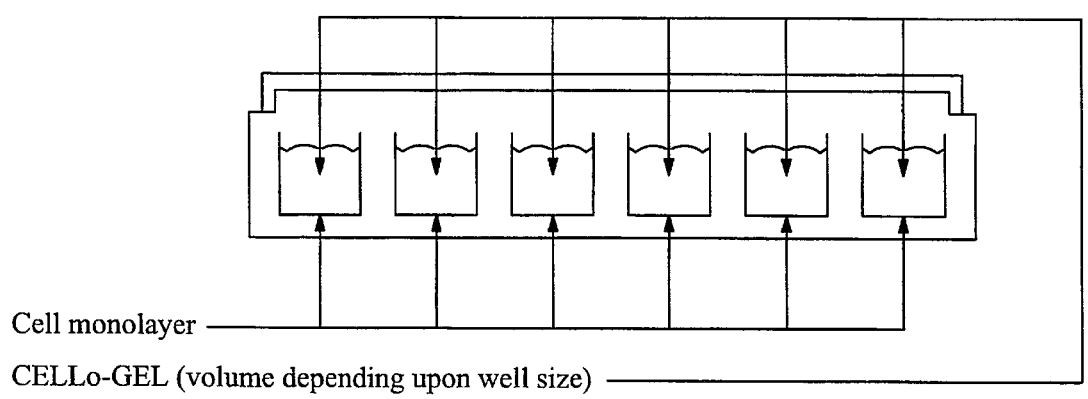
FIG. 1 shows a plan view of an example of a single 24 well plate in which four different cell systems may be transported.
FIG. 2 shows a side view of a 24 well plate which has been prepared for transport using the dual-state medium in accordance with the present invention.

The following detailed description is of the best presently contemplated mode of preparing and using the present invention. This description is not to be taken in a limiting sense, but is made merely for the purpose of illustrating the general principles of the invention. The scope of the invention is best defined by the appended claims.

The dual-state transport medium described below provides a source of protein for the growth, maintenance and transport of living cells in a pH balanced medium. Those skilled in the art will recognize that other nutritional media may be used as the basis for a dual-state transport medium in accordance with the present invention, with a primary requirement being that the nutritional media be compatible with the cell culture monolayer under study. The dual-state transport medium described below has been particularly effective for use with laboratory disciplines requiring cell cultures, and particularly virus laboratories. However, the skilled artisan will recognize that the present invention is generally applicable to any situation where cells in culture are utilized.

In the example described below, approximately 10.0 liters of a dual-state transport medium in accordance with the present invention may be produced by formulating the enumerated solutions as follows:

| SOLUTION 1: | |
| --- | --- |
| L-Tyrosine | 0.36 gm |
| L-Cystine | 0.24 gm |

Dissolve in approximately 200.0 ml of 0.075N Hydrochloric Acid with gentle heating to a maximum of about 80° C.

| SOLUTION 2: | |
| --- | --- |
| Nicotinamide | 0.2 gm |
| Pyridoxal | 0.2 gm |
| Thiamine | 0.2 gm |
| Pantothenic acid | 0.2 gm |
| Choline | 0.2 gm |
| i-Inositol | 0.4 gm |
| Riboflavin | 0.02 gm |

Dissolve in 175.0 ml distilled water and then to a final volume of 200.0 ml. Dispense in 10.0 ml aliquots and store at −20° C. It is preferred that ten (10.0) ml of SOLUTION 2 be prepared for every ten (10.0) liters of the dual-state transport medium.

SOLUTION 3

Dissolve 0.2 gm BIOTIN in 150.0 ml distilled water. To increase stability upon storage, 1.0 ml 1.0N Hydrochloric Acid may be added. Bring to a final volume of 200.0 ml with distilled water. Dispense in 10.0 ml aliquots and store at −20° C. It is preferred that ten (10.0) ml of SOLUTION 3 be prepared for every 10.0 liters of the dual-state transport medium.

SOLUTION 4

Dissolve 0.2 gm FOLIC ACID (crystalline) in 200.0 ml of HANKS balanced salt solution, pH 7.8. Dispense in 10.0 ml aliquots and store at −20° C. It is preferred that ten (10.0) ml of SOLUTION 4 be prepared for every 10.0 liters of the dual-state transport medium.

SOLUTION 5

Dissolve 2.0 gm anhydrous CALCIUM CHLORIDE in 160.0 ml distilled water. It is recommended that SOLUTION 5 be prepared shortly before use.

SOLUTION 6

Dissolve 12.0 gm L-GLUTAMINE in 400.0 ml distilled water and filter through a 0.2µ filter unit. Dispense in 100.0 ml aliquots and store at −20° C. It is preferred that one hundred (100.0) ml of SOLUTION 6 be prepared for every 10.0 liters of the dual-state transport medium.

SOLUTION 7

Dissolve 22.0 gm of sodium bicarbonate in 250.0 ml of distilled water and filter through a 0.2µ filter unit. It is recommended that SOLUTION 7 be used immediately after filtration.

SOLUTION 8

Dissolve 500.0 gm GELATIN (Type B: 225 Bloom) in one (1.0) liter distilled water. Gently heat to 56° C. It is preferred that one (1.0) liter of SOLUTION 8 be prepared for every 10.0 liters of the dual-state transport medium. Maintain liquid at 37° C. while adding to final 10.0 liters of the dual-state transport medium.

Using the solutions enumerated above, approximately 10.0 liters of a preferred dual-state transport medium may be prepared in accordance with the following procedure:

1. Add 68.0 gm of Sodium Chloride, 4.0 gm of Potassium Chloride, and 2.0 gm of Magnesium Sulfate ($MgSO_4 \cdot 7H_2O$) to SOLUTION 1. This creates a base mixture for the dual-state transport medium.
2. Dissolve 1.4 gm SODIUM PHOSPHATE MONOBASIC in 55.0 ml distilled water and add to the base mixture.
3. Dissolve 10.0 gm GLUCOSE in 50.0 ml distilled water and add to the base mixture.
4. Add 20.0 ml 1% PHENOL RED to the base mixture.
5. Bring the base mixture to 600.0 ml with distilled water.
6. Add 10.0 ml of SOLUTION 2 to the base mixture.
7. Add 10.0 ml of SOLUTION 3 to the base mixture.
8. Add 10.0 ml of SOLUTION 4 to the base mixture.
9. Add SOLUTION 5 slowly to the base mixture.
10. Add the following ingredients to the base mixture while stirring:

| Ingredient | Amount |
| --- | --- |
| Gentamycin sulfate | 0.5 gm |
| Streptomycin sulfate | 1.0 gm |
| Amphotericin B | 0.025 gm |
| L-Arginine HCl | 1.05 gm |
| L-Histidine HCl | 0.31 gm |
| L-Lysine HCl | 0.58 gm |
| L-Tryptophane | 0.10 gm |
| L-Phenylalanine | 0.32 gm |
| L-Threonine | 0.48 gm |
| L-Leucine | 0.52 gm |
| L-Valine | 0.46 gm |
| L-Isoleucine | 0.52 gm |
| L-Methionine | 0.15 gm |

11. Add distilled water to the base mixture to achieve a final volume of 1.0 liter.
12. Filter through a 0.2µ filter unit into sterile container sufficient to hold 10.0 liters.
13. Add the following ingredients aseptically while stirring:
   100.0 ml of SOLUTION 6
   250.0 ml of SOLUTION 7
   1,000.0 ml of SOLUTION 8
   1,000.0 ml of membrane filtered FETAL Bovine SERUM
   6,650.0 ml of sterile distilled water
14. While stirring, dispense into 500.0 ml aliquots.
15. Store in a refrigerator maintained at 4°–8° C. The solution will solidify below 28° C.
16. Prior to use, liquefy the dual-state transport medium at 37° C.
17. Dispense the dual-state transport medium into cell culture vessels when the medium is between 35°–37° C.

Vessels seeded with cells may be prepared for shipment by covering a cell monolayer with the above-described dual-state transport medium. A dual-state medium in accordance with the present invention may be applied to virtually any type of container (e.g. tubes, vials, multi-well plates, etc.) and virtually any type of cell (e.g. primary, diploid, heteroploid, etc).

The dual-state medium is advantageously used in conjunction with the sterile multi-well plates that are presently available from a number of different commercial sources. These sterile multi-well plates may vary in terms of shape and may vary in terms of the number of wells per plate (for example, such plates may contain 6, 12, 24, 48, or 96 wells). However, all such multi-well plates may be treated and handled in essentially the same way. Each multi-well plate is individually wrapped and sterile. In use, each plate is first removed from its package and kept closed until it is ready to be seeded with cells.

The cells to be transported are typically first grown in large flasks or other containers. At a stage in the growth process when transfer is appropriate, the cells are re-suspended in growth medium to the desired number (typically, approximately $10^5$ cells per ml per well) and transferred to the wells of the multi-well plate or other suitable container. Seeding of the desired number of cells is preferably accomplished under sterile conditions. The type of medium used on the cells prior to shipment may be of any composition that is consistent with adequate cell growth and the maintenance of good cell metabolism. Different wells or rows of wells may be seeded with different cell systems. When a cell monolayer is of acceptable density, as determined by the requirements of the recipient, seeded plates are ready for shipping.

Prior to shipping, growth or maintenance fluid may be removed and the dual-state transport medium in accordance with the present invention may be added in liquid form to thereby cover the cells. The amount of dual-state transport medium to be added may vary depending upon the size of the wells, although in a 24 well plate the amount per well would be approximately 1.0 ml.

The dual-state medium is then cooled to the point where it assumes a substantially solid form. The plate is then preferably put in a plastic envelope, sealed, and placed in a shipping container. A cooling material having a temperature of approximately −20° C. is added to the shipping container to maintain the temperature of the dual-state medium below 28° C. during shipment. The cooling material is preferably sufficient to maintain the dual-state transport medium in solid form during transport without freezing the cells. The shipping container may then be shipped by rapid carrier.

Upon arrival at the location of the end-user, the cells are incubated at a temperature of 35°–37° C. in a 5.0% $CO_2$ in air atmosphere to melt the gelatin. After warming, the dual-state transport medium may be removed and replaced with an appropriate volume of fresh maintenance medium. Alternatively, if the cells are not intended for immediate use upon receipt by the end user, the cells still covered with the dual-state medium in solid form may be stored at refrigerator temperature (4°–8° C.) for at least seven days. Prior to use, the cells in the solid state medium may be incubated at 35°–37° C. in a 5.0% $CO_2$ incubator for 4–8 hours to return the solid dual-state medium to liquid form. Cells shipped using a dual-state transport medium in accordance with the present invention are preferably used within one week.

Although the above-described example is directed to a procedure for sealing cells in wells of a multi-well plate to avoid leakage of liquid medium, the skilled artisan will recognize that a similar procedure may be used for all shipments of cells in wells or other containers in which leakage of culture medium might occur during transportation.

A dual-state medium in accordance with the present invention has been demonstrated to provide nutritional and physical support for fragile, sensitive, living cells during shipment and storage for at least seven days. Cells shipped by using the present invention may be used upon arrival in the diagnostic laboratory for disease diagnosis or in those laboratories requiring the immediate availability of live cells for research. The dual-state transport medium in accordance with the present invention enables cells to be transported in their most useful configuration and in well-type (or other "open") containers without spillage of the cell supporting medium. The dual-state transport medium in accordance with the present invention has been demonstrated to support cells frequently used in diagnostic laboratories (i.e. MRC-5 fetal human lung line; HF, human foreskin fibroblast line; A549, human lung carcinoma line; VERO, monkey kidney line and others).

The presently disclosed embodiment is therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for transporting animal cells, comprising:

providing a layer of cells in a first medium in a container, providing a second medium which assumes a liquid state above a first temperature and a solid state below a second temperature, covering the layer of cells in the first medium with a layer of the second medium in a liquid state, reducing the temperature of the second medium to a temperature at which the second medium assumes a solid state, maintaining the second medium in a solid state while transporting the cells in the first medium, increasing the temperature of the second medium to a temperature at which the second medium assumes a liquid state, and removing at least a portion of the second medium from the layer of cells in the first medium.

2. The method of claim 1 wherein the step of providing the cells in a first medium in a container comprises providing the cells in a first medium in at least one well of a multi-well plastic plate.

3. The method of claim 1 wherein the first temperature is between approximately 35° C. and 37° C. and wherein the second temperature is below approximately 28° C.

4. The method of claim 1 wherein the step of maintaining the second medium in a solid state while transporting the cells in the first medium comprises providing a cooling material that is sufficient to maintain the second medium in a solid state without freezing the cells in the first medium.

5. The method of claim 4 wherein the step of providing a cooling material that is sufficient to maintain the second medium in a solid state without freezing the cells in the first medium comprises providing a cooling material having a temperature of approximately −20° C.

6. The method of claim 1 wherein the step of increasing the temperature of the second medium to a temperature at which the second medium assumes a liquid state comprises incubating the cells in the first medium at a temperature of between approximately 35° C. to 37° C. in an air atmosphere of approximately 5.0% $CO_2$.

7. The method of claim 1 comprising the step of storing the cells in the first medium covered with the second medium at a temperature of between approximately 4° C. and 8° C.

8. The method of claim 7 wherein the step of increasing the temperature of the second medium to a temperature at which the second medium assumes a liquid state comprises incubating the cells in the first medium at a temperature of between approximately 35° C. to 37° C. in an air atmosphere of approximately 5.0% $CO_2$.

9. A system for transporting animal cells, comprising:

a container for receiving a layer of cells in a first medium, a second medium layer for covering the layer of cells in the first medium in the container, the second medium assuming a liquid state above a first temperature and a solid state below a second temperature, and means for maintaining the second medium in a solid state while transporting the layer of cells in the first medium.

10. The system of claim 9 wherein the container comprises a multi-well plastic plate.

11. The system of claim 9 wherein the first temperature is between approximately 35° C. and 37° C. and wherein the second temperature is below approximately 28° C.

12. The system of claim 9 wherein the means for maintaining the second medium in a solid state while transporting the cells in the first medium comprises a cooling material that is sufficient to maintain the second medium in a solid state without freezing the cells in the first medium.

13. The system of claim 12 wherein the cooling material has a temperature of approximately −20° C.

14. A system for transporting animal cells, comprising;

a plate having a plurality of wells containing a layer of cells in a first medium, a nutritional second medium layer for covering the layer of cells in the first medium in at least one of the plurality of wells and for protection, maintenance and transport of the cells in the first medium in at least one of the plurality of wells, the second medium assuming a liquid state above a first temperature and a solid state below a second temperature, both the first and second temperatures being compatible with survival of the cells in the first medium in at least one of the plurality of wells.

* * * * *